(12) United States Patent
Oshima

(10) Patent No.: US 8,932,062 B2
(45) Date of Patent: Jan. 13, 2015

(54) BODY WEIGHT MANAGEMENT DEVICE

(75) Inventor: Yoshitake Oshima, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/991,215

(22) PCT Filed: Nov. 28, 2011

(86) PCT No.: PCT/JP2011/077366
§ 371 (c)(1),
(2), (4) Date: Jun. 3, 2013

(87) PCT Pub. No.: WO2012/111214
PCT Pub. Date: Aug. 23, 2012

(65) Prior Publication Data
US 2013/0252211 A1    Sep. 26, 2013

(30) Foreign Application Priority Data

Feb. 16, 2011 (JP) ................................. 2011-030776

(51) Int. Cl.
| | |
|---|---|
| G09B 19/00 | (2006.01) |
| G01G 19/50 | (2006.01) |
| G06Q 50/22 | (2012.01) |
| G06Q 10/06 | (2012.01) |
| A61B 5/053 | (2006.01) |
| G06F 19/00 | (2011.01) |

(52) U.S. Cl.
CPC ............ G09B 19/0092 (2013.01); G01G 19/50 (2013.01); G06Q 50/22 (2013.01); G06Q 10/06 (2013.01); A61B 5/0537 (2013.01); G06F 19/3475 (2013.01); G06F 19/3406 (2013.01)

USPC .......................................................... 434/127

(58) Field of Classification Search
USPC ................................................. 434/127, 247
See application file for complete search history.

(56) References Cited

U.S. PATENT DOCUMENTS

2011/0301916 A1* 12/2011 Oshima et al. ................ 702/173

FOREIGN PATENT DOCUMENTS

| | | |
|---|---|---|
| JP | 09-021689 A | 1/1997 |
| JP | 2002-083054 A | 3/2002 |
| JP | 2004-135756 A | 5/2004 |

(Continued)

OTHER PUBLICATIONS

Official Communication issued in International Patent Application No. PCT/JP2011/077366, mailed on Feb. 28, 2012.

*Primary Examiner* — Kesha Frisby
(74) *Attorney, Agent, or Firm* — Keating & Bennett, LLP

(57) ABSTRACT

A body weight management device includes a body weight obtainment unit that obtains measurement data in which a body weight measurement value and a measurement day/time are associated with each other, an increase/decrease amount calculation unit that calculates a target intra-day variation amount by which the body weight varies during sleep, a target obtainment unit that calculates a target value when measuring a pre-sleep body weight value at a second timing before the measurement subject sleeps relative to a post-waking body weight value that is measured at a first timing after the measurement subject wakes, an advice obtainment unit that obtains advice information regarding meals to achieve the target value, based on a result of comparing a pre-meal body weight value measured at a third timing prior to a meal with a threshold value, and an output processing unit that outputs the obtained advice information.

13 Claims, 11 Drawing Sheets

(56) References Cited

FOREIGN PATENT DOCUMENTS

| | | | |
|---|---|---|---|
| JP | 2005-296303 A | 10/2005 |
| JP | 2005-319216 A | 11/2005 |
| JP | 2006-252150 A | 9/2006 |
| JP | 2009-189443 A | 8/2009 |
| JP | 2009-289096 A | 12/2009 |
| JP | 2010-086213 A | 4/2010 |
| JP | 2010-181377 A | 8/2010 |
| JP | 2010-237805 A | 10/2010 |

* cited by examiner

FIG. 4A

| 403 | MEASUREMENT DATE | JANUARY 26 | | JANUARY 27 | | JANUARY 28 | | JANUARY 29 | | JANUARY 30 | | JANUARY 31 | |
|---|---|---|---|---|---|---|---|---|---|---|---|---|---|
| 404 | FLAG | ☀ | ☾ | ☀ | 🥄 | ☀ | 🥄 | ☀ | 🥄 | ☀ | 🥄 | ☀ | ☾ |
| 403 | MEASUREMENT TIME | 6:45 | 19:50 | 6:45 | 19:40 | 6:30 | 19:30 | 7:00 | 19:40 | 6:30 | 18:30 | 6:45 | 19:30 |
| 401 | BODY WEIGHT (kG) | 51.2 | 51.0 | 51.3 | 51.3 | 51.5 | 51.1 | 51.0 | 51.0 | 50.8 | 50.8 | 50.7 | 51.2 |
| 405A | INTRA-DAY CHANGE AMOUNT | 0.4 | | 0.7 | | 0.5 | | 0.3 | | 0.3 | | | |
| 405B | EVENING MEAL CHANGE AMOUNT | | 0.6 | | 0.7 | | 0.9 | | 0.3 | | 0.3 | | |
| 405C | NIGHTTIME CHANGE AMOUNT | | | | -0.3 | | -0.5 | | -1 | | -0.5 | | -0.4 |
| 406 | ACHIEVEMENT EVALUATION | OK | | NG | | OK | | OK | | OK | | — | |

FIG. 4B
41 — STANDARD INTRA-DAY VARIATION AMOUNT | 576g

FIG. 4C
42 — TARGET SETTING DAY | 2009/1/26

FIG. 4D
43 — LONG-TERM TARGET INCREASE/DECREASE AMOUNT | -4kg

FIG. 4E
44 — TARGET ACHIEVEMENT PERIOD | 3 months

FIG. 4F
45 — INTRA-DAY TARGET INCREASE/DECREASE AMOUNT | -44.4g

FIG. 4G
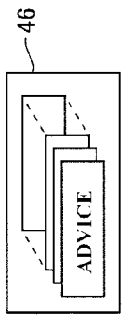

MORNING-EVENING BODY WEIGHT CHANGE

INTRA-DAY VARIATION

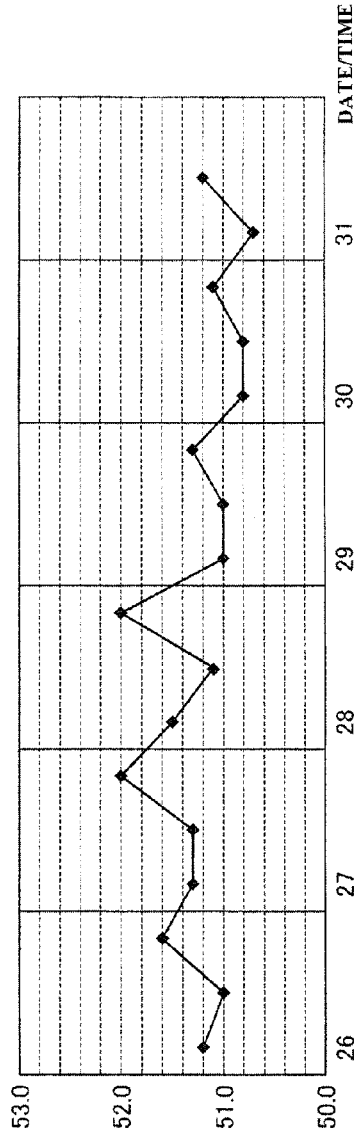
FIG.8A
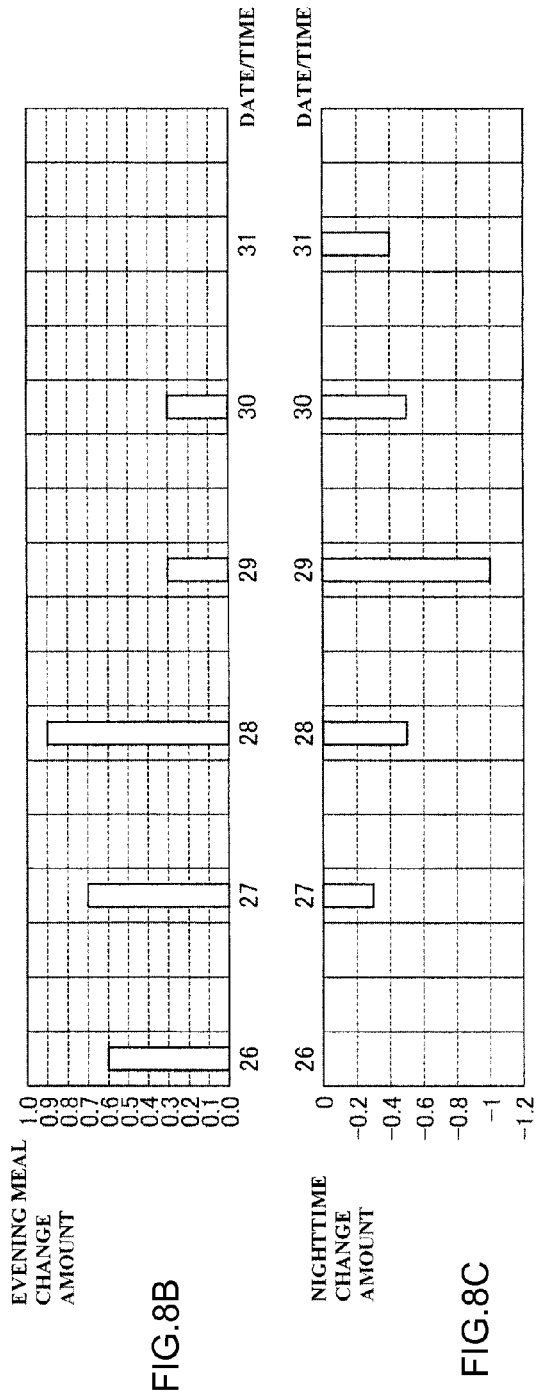
FIG.8B
FIG.8C

FIG. 10

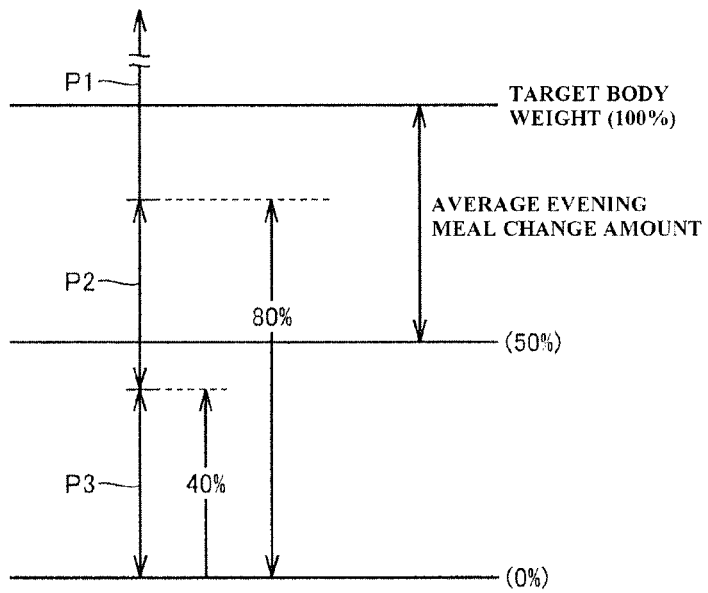

FIG.11A
M1: IT LOOKS LIKE YOU WILL GO OVER YOUR TARGET IF YOU EAT THE USUAL AMOUNT AT YOUR EVENING MEAL. YOU WILL NEED TO CUT BACK ON YOUR EVENING MEAL AMOUNT, OR EXERCISE AFTER EATING.

FIG.11B
M2: IT LOOKS LIKE YOU WILL ACHIEVE YOUR TARGET AT THIS PACE. TAKE CARE NOT TO OVEREAT, AND BE SURE TO EAT AN APPROPRIATE AMOUNT.

FIG.11C
M3: YOU ARE IN A GOOD PATTERN. YOU WILL ALSO NEED TO TAKE CARE NOT TO LOSE TOO MUCH WEIGHT.

DISPLAY EXAMPLE FOR
MORNING MEASUREMENT

RESULT (MORNING)

50.7 kg

--------------------

51.3 kg

EVENING TARGET

DISPLAY EXAMPLE FOR
PRE-EVENING MEAL
MEASUREMENT

RESULT
(PRE-EVENING MEAL)

51.2 kg

--------------------

EVENING MEAL ADVICE

IT LOOKS LIKE YOU WILL GO
OVER YOUR TARGET IF YOU
EAT THE USUAL AMOUNT AT
YOUR EVENING MEAL.
YOU WILL NEED TO CUT
BACK ON YOUR EVENING
MEAL AMOUNT, OR EXERCISE
AFTER EATING.

BODY WEIGHT MANAGEMENT DEVICE

BACKGROUND OF THE INVENTION

1. Field of the Invention

The present invention relates to body weight management devices, and particularly relates to body weight management devices that present dietary advice based on a measurement subject's body weight that varies during the day.

2. Description of the Related Art

Conventionally, a measurement subject can manage his or her weight while confirming whether his or her body weight is increasing or decreasing by measuring his or her body weight using a scale.

JP 2009-289096A discloses a system in which a third party comprehensively manages a target person's body weight. With this system, an email containing advice regarding body weight management that draws on the knowledge and experience of a counselor is sent to the target person based on changes in the body weight measured by the target person.

Increased health consciousness in recent years has led to demand for body weight management advice that takes into consideration intra-day body weight variations to be presented every day in order to effectively facilitate body weight management such as weight loss. However, with JP 2009-289096A, the target person records his/her measured body weight for no less than a set number of days and sends the recorded data to the counselor, whereupon the counselor analyzes the data and returns his/her advice, and thus this technique has not been able to meet the aforementioned demand.

SUMMARY OF THE INVENTION

In light of this, preferred embodiments of the present invention provide a body weight management device that outputs dietary information so that a target value can be achieved, while taking intra-day variation in the body weight into consideration.

A body weight management device according to a preferred embodiment of the present invention includes a body weight obtainment unit that obtains measurement data in which a body weight measurement value for a measurement subject and a measurement day/time are associated with each other; an increase/decrease amount calculation unit that calculates a target intra-day change amount using an amount by which the body weight varies during sleep based on the measurement data; a target obtainment unit that, based on the target intra-day change amount, calculates a target value when measuring a pre-sleep body weight value at a second timing before the measurement subject sleeps relative to a post-waking body weight value that is measured at a first timing after the measurement subject wakes; an advice obtainment unit that obtains advice information regarding meals to achieve the target value, based on a result of comparing a pre-meal body weight value measured at a third timing prior to a meal with a threshold value; and an output unit that outputs the obtained advice information.

According to a preferred embodiment of the present invention, information of meals that enable a target value to be achieved while taking into consideration intra-day variations in the body weight can be provided.

The above and other elements, features, steps, characteristics and advantages of the present invention will become more apparent from the following detailed description of the preferred embodiments with reference to the attached drawings.

BRIEF DESCRIPTION OF THE DRAWINGS

FIGS. 4A through 4G are diagrams illustrating various types of data held in a storage unit according to a preferred embodiment of the present invention.

FIGS. 8A through 8C are diagrams illustrating body weight change amounts according to a preferred embodiment of the present invention.

FIG. 10 is a diagram illustrating a meal amount determination according to a preferred embodiment of the present invention.

FIGS. 11A through 11C are diagrams illustrating examples of advice according to a preferred embodiment of the present invention.

FIGS. 12A and 12B are diagrams illustrating a display example during pre-meal body weight measurement according to a preferred embodiment of the present invention.

DETAILED DESCRIPTION OF THE PREFERRED EMBODIMENTS

Figure 1:
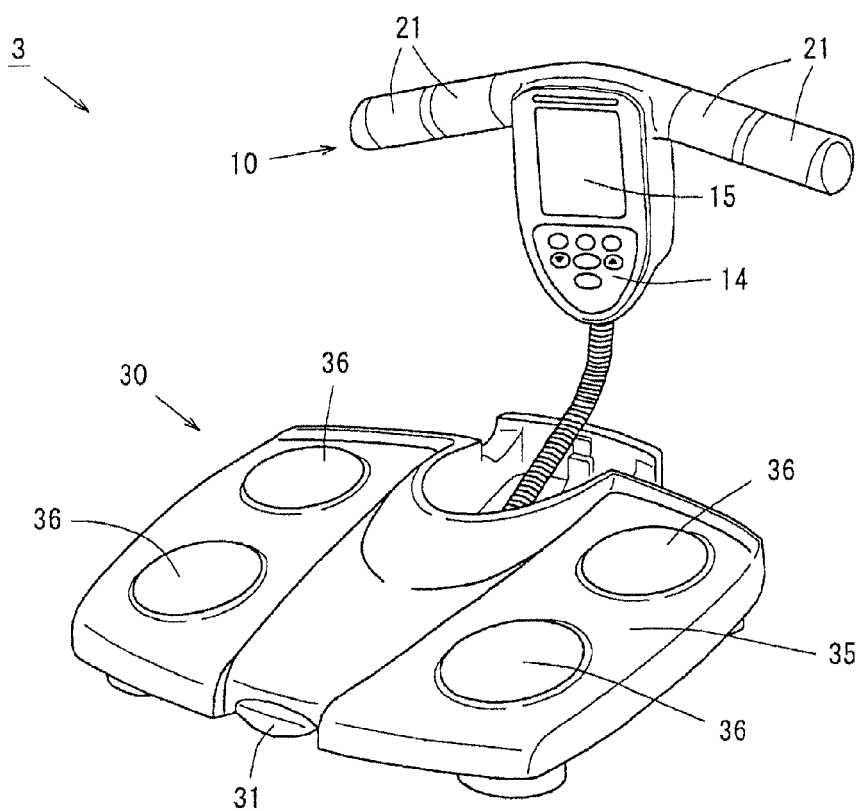
FIG. 1 is a perspective view illustrating the external appearance of a body composition meter according to a preferred embodiment of the present invention.

Hereinafter, preferred embodiments of the present invention will be described in detail with reference to the drawings. Note that in the following preferred embodiments, identical or corresponding elements are given the same reference numerals in the drawings, and descriptions thereof will not be repeated.

First, definitions will be given for terms. In the present preferred embodiment, "morning time" refers, with respect to body weight measurement, to a period of time spanning from, for example, 4 AM to noon (12 PM), whereas "evening time" refers to a period of time spanning from, for example, 7 PM to 2 AM. "Morning body weight" refers to a body weight measured during the morning time, whereas "evening body weight" refers to a body weight measured during the evening time.

In the present preferred embodiment, "sleeping time" refers to a time when the evening body weight is measured, whereas "waking time" refers to a time when the morning body weight is measured. In the present preferred embodiment, body weight measurements are taken multiple times in a single day, but it is assumed that during a single day, the body weight is measured at least at a timing closer to waking, at a timing closer to sleeping, and at a pre-meal timing. To simplify the descriptions, it is assumed that the body weight is measured immediately before going to bed (evening body weight) for sleeping, the body weight is measured immediately after waking up (morning body weight), and that a body weight measurement is performed prior to an evening meal. Note that "intra-day" refers to a single day, from the waking time to the sleeping time of a measurement subject.

"Nighttime body weight decrease" refers to a decrease in body weight caused primarily by basal metabolism, such as perspiration, occurring during the period from the sleeping time to the waking time. "Intra-day target increase/decrease amount" refers to a body weight increase/decrease amount to be used as a target during a single day. "Target intra-day change amount" refers to an amount of change in the body weight composed of the "nighttime body weight decrease" and the "intra-day target increase/decrease amount".

"Pre-evening meal time" refers to a time prior to eating a meal before measuring the evening body weight, or in other words, prior to the evening meal. "Pre-evening meal body weight" refers to a body weight measured at the pre-evening meal time.

In the present preferred embodiment, a body weight/body composition meter capable of obtaining not only a body weight but also a given type of body composition information, such as a body fat percentage, by measuring a body impedance, is illustrated as an example of a body weight management device, but a device that only has a function to measure a body weight may be used as well.

Figure 2:
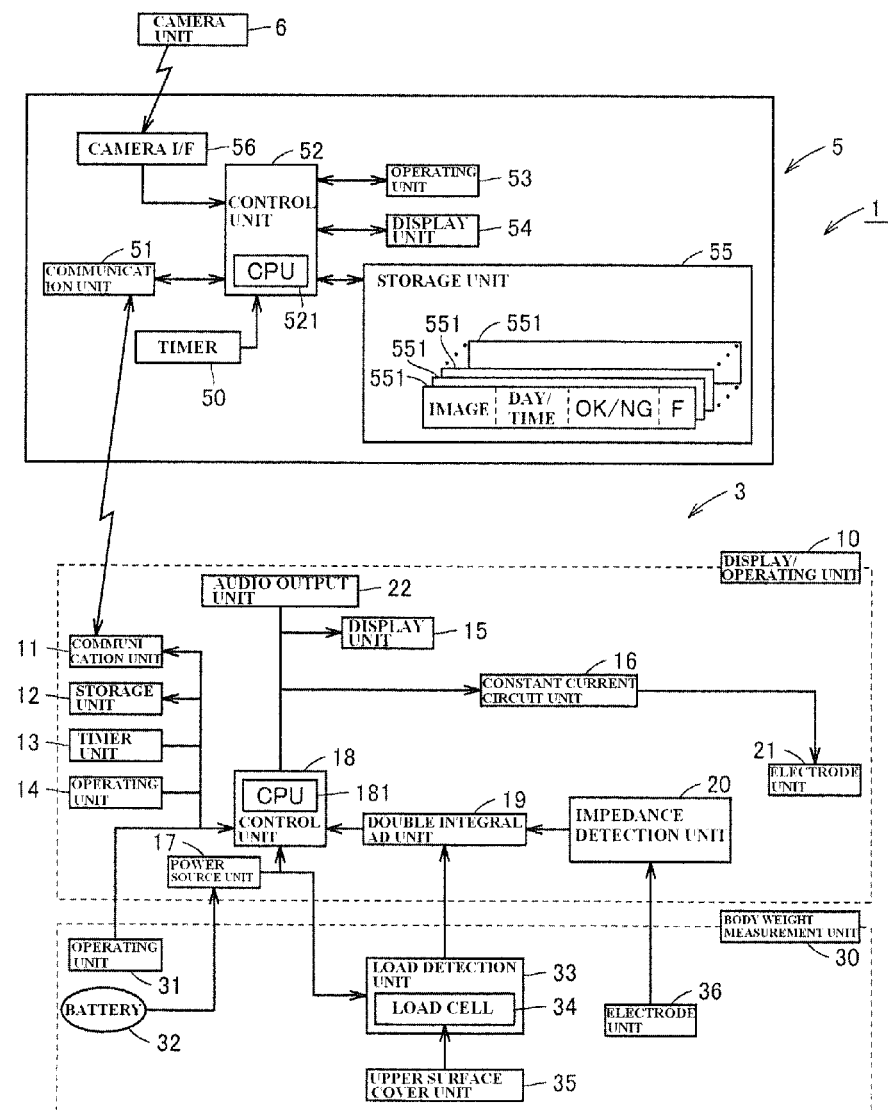
FIG. 2 is a block diagram illustrating the configuration of the body composition meter and a server according to a preferred embodiment of the present invention.

FIG. 1 illustrates the external appearance of a body weight/body composition meter 3, whereas FIG. 2 illustrates the configuration of a body weight management system 1.

The body weight management system 1 shown in FIG. 2 includes the body weight/body composition meter 3 and a server (server computer) 5 that communicates, wirelessly or over wires, with the body weight/body composition meter 3 and an external camera unit 6. To simplify the descriptions, FIG. 2 illustrates a single body weight/body composition meter 3 being connected to the server 5, but multiple body weight/body composition meters 3 may be connected to the server 5, for example. Note that the exchange of data between the body weight/body composition meter 3 and camera unit 6 and the server 5 is not limited to communications, and the exchange may take place via a storage medium.

As shown in FIG. 1, the body weight/body composition meter 3 includes a display/operating unit 10, which includes a first housing member held by a measurement subject's hand, and a body weight measurement unit 30, which is a second housing member onto which the measurement subject steps.

The display/operating unit 10 includes, as shown in FIG. 2, a communication unit 11, a storage unit 12, a timer unit 13, an operating unit 14, a display unit 15, a constant current circuit unit 16, a power source unit 17, a control unit 18 that includes a CPU (central processing unit) 181, a double integral AD (analog/digital) unit 19, an impedance detection unit 20, electrode units 21, and an audio output unit 22.

The communication unit 11 is connected to the control unit 18, and communicates with the server 5 in accordance with a control signal from the control unit 18. Note that the communication unit 11 is not limited to communicating with the server 5; the communication unit 11 may communicate with any appropriate device, including another body information obtainment device such as a pedometer or the like, or a personal computer, mobile information terminal (a PDA (personal digital assistant), a mobile telephone, or the like), and so on.

The storage unit 12 includes an apparatus that can store information, such as a non-volatile memory, a hard disk, or the like. The storage unit 12 has information read out therefrom and written thereto in accordance with a control signal from the control unit 18, to which the storage unit 12 is connected.

The timer unit 13 is a device including a timer/counter that measures an amount of time from the present day/time, and outputs a measured amount of time to the control unit 18 as necessary.

The operating unit 14 includes multiple buttons/switches and the like (see FIG. 1) that are operated by being depressed or the like. By manipulating the operating unit 14, the measurement subject can input his/her personal information/body information, such as an ID, sex, age, height, body weight, and so on. The inputted information is outputted to the control unit 18.

The display unit 15 includes a display device such as a liquid-crystal display (see FIG. 1), and displays images such as text, graphics, or the like in accordance with an image signal supplied from the control unit 18.

The constant current circuit unit 16 applies a high-frequency (AC) current supplied from the power source unit 17 to current application electrode units 21 in a single direction, under the control of the control unit 18. The power source unit 17 supplies operational electricity to the respective elements, including the control unit 18.

The control unit 18 preferably includes a microcomputer that includes the CPU 181, a ROM (read-only memory), and a RAM (random access memory) (not shown), and is programmed to execute control operations and computational operations for the respective constituent elements in accordance with programs and various types of data stored in the ROM or the like. These programs and data include programs and data for body weight management.

The double integral AD unit 19 is a double integral-type AD conversion unit. During operations, the double integral AD unit 19 converts an analog signal (a voltage signal) outputted from the impedance detection unit 20 into a digital signal and outputs that digital signal to the control unit 18.

The impedance detection unit 20 detects a body impedance of the measurement subject based on a potential difference between electrode units 36 provided in the body weight measurement unit 30 and the electrode units 21 provided in the display/operating unit 10.

The electrode units 21 are preferably provided on the surfaces of grip portions (see FIG. 1) in the display/operating unit 10, which are held in the measurement subject's hand. The electrode units 21 apply the high-frequency (AC) current, supplied from the power source unit 17, to the palms of the measurement subject's hands that are gripping the grip portions.

The body weight measurement unit 30 includes an operating unit 31, a battery 32, a load detection unit 33, and the electrode units 36. The operating unit 31 functions as an input switch that is manipulated in order to switch the power on or off, and when the operating unit 31 is manipulated, an input signal is outputted to the control unit 18 in response to that manipulation.

The battery 32 supplies power to the respective elements, and in particular, to the power source unit 17.

The load detection unit 33 includes multiple load cells 34 provided therein. The load detection unit 33 measures the body weight of the measurement subject that has stepped onto an upper surface cover unit 35 (see FIG. 1) that also serves as an upper surface cover of the housing member. The measured body weight is outputted to the double integral AD unit 19.

The electrode units 36 are provided in the surface of the upper surface area of the body weight measurement unit 30 (see FIG. 1) onto which the measurement subject steps, and serve as current measurement electrodes that detect a current that flows from the soles of the measurement subject's feet. The electrode units 36 preferably include four electrodes that make contact with the left toe side, the left heel side, the right toe side, and the right heel side of the measurement subject's feet, for example.

Each of the load cells 34 in the load detection unit 33 is disposed so as to be capable of measuring a load placed on the upper surface area of the body weight measurement unit 30, and here, are disposed below the respective electrodes in the electrode units 36. Accordingly, both the body impedance and the body weight can be measured when the measurement subject steps upon the upper surface area.

During body weight measurement, a load produced by the measurement subject's body weight is exerted on the load cells 34. Each of the load cells 34 preferably includes a bending member, formed of a metal member that deforms in response to a load exerted thereon, and a strain gauge that is applied to the bending member. When the bending member bends, the strain gauge extends/contracts, and a resistance value changes in accordance with the extension/contraction of the strain gauge; the change in resistance is then obtained as a load signal output. Accordingly, in the case where the measurement subject has stepped onto the upper surface area and both feet have been placed on the load cells 34, the bending member will bend due to the measurement subject's body weight that has been applied to the load cells 34, and the body weight will be measured as a change in the aforementioned load signal output.

Although the load cells 34 are preferably used in the present preferred embodiment as load sensors to detect a load, it should be noted that a sensor that includes, for example, springs, a piezoelectric film, or the like, a compression element, a displacement sensor, or the like may be used as long as that element is capable of detecting the amount of a force applied to the upper surface area.

The server 5 includes a timer 50 that measures the present time, a communication unit 51 that communicates with the body weight/body composition meter 3, a control unit 52 including a computer having a CPU 521, a ROM, and a RAM, an operating unit 53, a display unit 54, storage unit 55, and a camera I/F (interface) 56 that communicates with the camera unit 6. Here, it is assumed that the timer 50 and the timer unit 13 are adjusted so as to perform time measurement operations in synchronization with each other.

The communication unit 51 exchanges data with the body weight/body composition meter 3 under the control of the control unit 52. The CPU 521 of the control unit 52 is programmed to control the operations of the respective elements and executes various types of computations in accordance with programs and data stored in the ROM or the like.

The operating unit 53 preferably includes a keyboard, a mouse, or the like. Signals inputted as a result of operations performed by an operator are outputted to the control unit 52.

The display unit 54 corresponds to a liquid-crystal display, a CRT (cathode ray tube) display, or the like. The display unit 54 displays images such as graphics, text, or the like in accordance with a control signal supplied from the control unit 52.

The storage unit 55 corresponds to a fixed storage device such as a hard disk, or a recording medium that can be read by the computer that includes the CPU 521, such as a flexible disk, a CD-ROM (compact disk read-only memory), a ROM (read-only memory), a RAM (random access memory), a memory card, and so on.

The storage unit 55 stores data measured by the body weight/body composition meter 3 (body composition information, body weight data, measurement day/time data, and so on), various types of data related to the measurement subject, including the personal information such as the measurement subject's name (ID), address, and so on, as well as records 551, which will be mentioned later.

Figure 3:
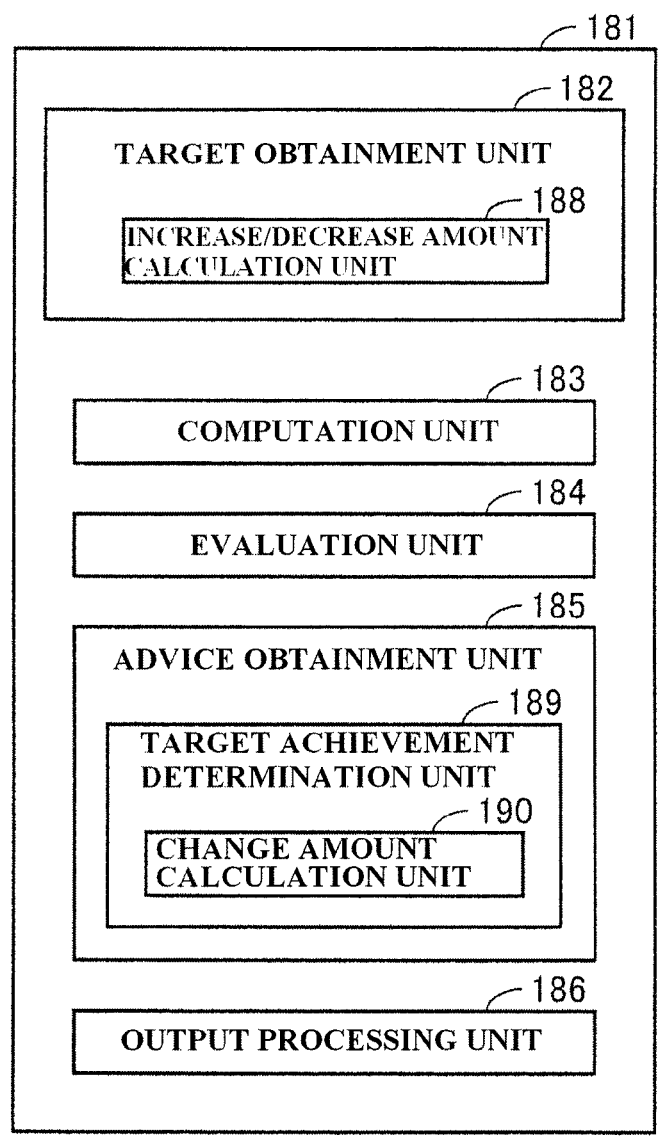
FIG. 3 is a diagram illustrating the functional configuration of a control unit according to a preferred embodiment of the present invention.

The functional configuration of the body weight/body composition meter 3, as related to body weight management, will be described with reference to FIG. 3. The CPU 181 includes a target obtainment unit 182, a computation unit 183, an evaluation unit 184 that evaluates a target achievement level, an advice obtainment unit 185 that obtains advice regarding body weight management, and an output processing unit 186 that outputs a measurement result and advice through a display or as audio. These elements are realized by programs executed by the CPU 181. These programs are stored in advance in the ROM (not shown) of the control unit 18. The functions of the respective elements are realized by the CPU 181 reading out the programs from the ROM and executing the commands in the read-out programs.

The target obtainment unit 182 obtains a target intra-day change amount for a body weight value, including a nighttime body weight decrease, which is the amount of change in the body weight value during sleep, and the intra-day target increase/decrease amount of the body weight value. The target obtainment unit 182 includes an increase/decrease amount calculation unit 188. Based on the target intra-day change amount obtained by the target obtainment unit 182, an intra-day target value (called an "evening target body weight" hereinafter) to serve as a target to be achieved is calculated when a pre-sleep body weight value is measured at a second timing near when the measurement subject sleeps (that is, the evening time), based on a post-waking body weight value measured at a first timing after the measurement subject has woken up (that is, the morning time). The increase/decrease amount calculation unit 188 calculates the intra-day target increase/decrease amount, which will be described later.

The advice obtainment unit 185 includes a target achievement determination unit 189. The target achievement determination unit 189, meanwhile, includes a change amount calculation unit 190 that calculates an amount of change in the measured body weight.

The various types of data held in the storage unit 12 will be described in detail with reference to FIGS. 4A through 4G. Body weights measured using the body weight measurement unit 30 are managed using records 40. The storage unit 12 has a capacity that enables multiple weeks' worth or multiple months' worth of records 40 to be stored.

Each of the records 40 holds data 401 indicating actually-measured body weight values, data 403 specifying a date/time of body weight measurement based on time measurement data from the timer unit 13 in association with each piece of data 401, and flags 404. Each of the records 40 further holds associated data 405A, 405B, and 405C indicating body weight change amounts calculated based on the body weights in the data 401 and achievement evaluation data 406 indicating a result of evaluating the target achievement level.

The flags 404 include flags specifying whether the body weight indicated by the corresponding data 401 corresponds to a morning body weight, an evening body weight, or a pre-meal body weight. Specifically, a sun symbol corresponds to a flag indicating the morning body weight, a spoon symbol corresponds to a flag indicating the pre-meal body weight, and a moon symbol corresponds to a flag indicating the evening body weight.

Standard intra-day variation amount data 41, shown in FIG. 4B, indicates a standard intra-day change amount for the measurement subject. This standard intra-day change amount is calculated by the computation unit 183 based on the records 40 that hold past measurement data (that is, one weeks' worth or two weeks' worth). This calculation may be carried out as follows.

That is, a nighttime body weight decrease indicating a variation in the body weight during sleep is calculated by subtracting the next day's morning body weight from the previous evening body weight; this nighttime body weight decrease is calculated over multiple days, the average value thereof is calculated, and that average value is taken as the standard intra-day change amount.

As another method for calculating the standard intra-day change amount, it should be noted that the computation unit 183 can use a basal metabolism amount (Kcal) determined based on the measurement subject's body impedance as detected by the impedance detection unit 20. Note that the method for calculating the basal metabolism amount uses a known procedure. Generally, 9 Kcal is required to burn 1 g of fat (however, because human fat contains 20% water, this number is approximately 7 Kcal), 4 Kcal is required to burn 1 g of carbohydrate, and 4 Kcal is required to burn 1 g of protein; accordingly, the computation unit 183 can calculate the nighttime body weight decrease amount based on these consumed Kcal amounts, the calculated basal metabolism amount, and a sleep time (the total amount of time from the sleeping time to the waking time). This nighttime body weight decrease is calculated over multiple days, the average value thereof is calculated, and that average value can then be taken as the standard intra-day change amount.

Note that the standard intra-day change amount is not limited to being calculated for each measurement subject, and a fixed value can be set for the intra-day change amount of a typical person set in advance.

Target setting day data 42 is indicated in FIG. 4C. The target setting day data 42 indicates the date at which the measurement subject started body weight management such as a diet using the body weight/body composition meter 3, and indicates a date inputted by the measurement subject operating the operating unit 14.

Long-term target increase/decrease amount data 43, shown in FIG. 4D, indicates a target value for a body weight increase/decrease amount, inputted by the measurement subject manipulating the operating unit 14. For example, a negative value is inputted in the case where the measurement subject wishes to lose weight, 0 is inputted in the case where the measurement subject wishes to maintain his/her body weight, and a positive value is inputted in the case where the measurement subject wishes to gain weight. Note that this value may be a target body weight value instead of an increase/decrease amount.

Target achievement period data 44, shown in FIG. 4E, indicates a target achievement period set by the measurement subject operating the operating unit 14. The target achievement period indicates a period by the end of which the long-term target increase/decrease amount is to be achieved.

When this target achievement period is inputted and set, the target obtainment unit 182 determines, as appropriate, whether or not an intra-day increase/decrease amount that serves as a daily norm, obtained by dividing the long-term target increase/decrease amount by the number of days of the target achievement period, falls within a predetermined range. In the case where it is determined that the amount is outside of the predetermined range, an error display is made in the display unit 15. The measurement subject is then prompted to re-input the target achievement period until the amount is determined to fall within the predetermined range. Through this, an excessive diet that places a burden on the measurement subject's body or the like can be avoided.

With respect to body weight variations, experiments performed by the inventors indicated that for a healthy adult, a weight loss (or gain) for one month that is an increase/decrease percentage of the present body weight within the predetermined range, or in other words, within about 2% to about 10%, for example, will not be unhealthy. Accordingly, the present preferred embodiment is set so that the decrease amount (or increase amount) over one month is an amount that is about 2% to about 10%, for example, of the present body weight.

Intra-day target increase/decrease amount data 45, indicated in FIG. 4F, is set to a value calculated by the increase/decrease amount calculation unit 188 dividing the long-term target increase/decrease amount by the target achievement period. Based on this intra-day target increase/decrease amount data 45, it is possible to confirm whether or not the body weight increase/decrease is progressing according to the target on a daily basis, calculate the evening target body weight for that day, and so on.

Advice data 46 indicated in FIG. 4G is referred to (read out) by the advice obtainment unit 185. Here, each piece of advice indicated in the advice data 46 is assumed to be stored in the storage unit 12 in a pre-edited state, but the configuration may be such that the advice obtainment unit 185 edits the data.

Here, a method for calculating the evening target body weight in the case where body weight management for the purpose of dieting (that is, losing weight) is carried out, will be described with reference to FIGS. 5A and 5B.

Figure 5A:
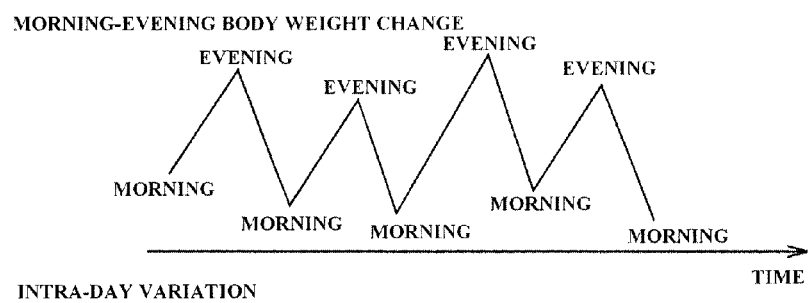
FIGS. 5A and 5B are diagrams illustrating an outline of target nighttime body weight calculation according to a preferred embodiment of the present invention.
Figure 5B:
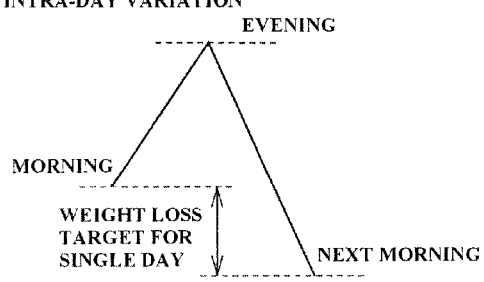

As shown in FIG. 5A, generally, the measurement subject's morning body weight and evening body weight vary during a single day. Looking at the intra-day variations shown in FIG. 5A, the morning body weight is a body weight measured after waking up and can thus be taken as the minimum body weight for that day; thus, as shown in FIG. 5B, the difference between the morning body weight for that day and the morning body weight for the next day can be determined as the amount that should be adjusted, or in other words, as a target weight loss for a single day. Accordingly, the evening target body weight for that day can be calculated by adding the target weight loss for a single day to the morning body weight of that day.

In the present preferred embodiment, the target weight loss for a single day is taken as the target intra-day change amount, and the target intra-day change amount is calculated by adding the standard intra-day change amount (the "nighttime body weight decrease" average) in the data 41 to the "intra-day target increase/decrease amount" in the data 45.

Figure 6:
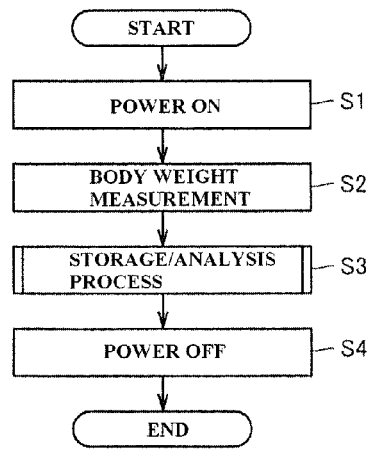
FIG. 6 is a main flowchart according to a preferred embodiment of the present invention.
Figure 7:
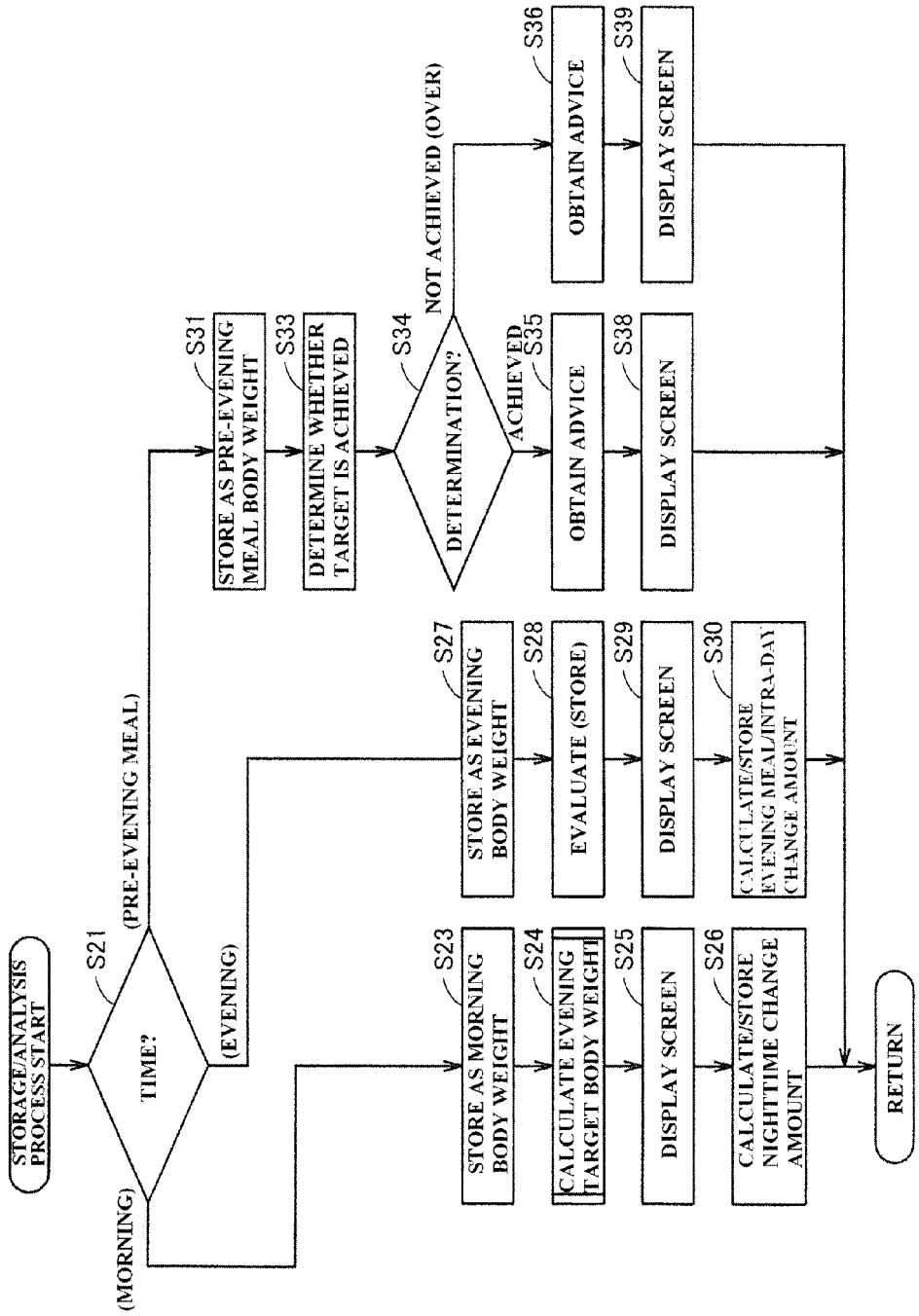
FIG. 7 is a flowchart illustrating a storage/analysis process according to a preferred embodiment of the present invention.

FIGS. 6 and 7 are flowcharts illustrating operations executed by the CPU 181 in the control unit 18 of the body weight/body composition meter 3. Here, processes for executing body weight management according to the present preferred embodiment will be described based on these flowcharts. These flowcharts are held in a memory in the control unit 18 or the storage unit 12 in advance as programs, and the processes are realized by the CPU 181 reading out the programs and executing the commands contained therein.

Note that the data 41 through the data 46 shown in FIGS. 4A through 4G are assumed to be held in the storage unit 12 in advance. In addition, it is assumed that, for example, five days' worth of records 40 from the date specified in the target setting day data 42 is held in the storage unit 12. Thus, descriptions will be given assuming that the body weight measurement for the sixth day is being carried out here. In addition, it is assumed that the measurement subject measures his/her body weight every day at the morning time, pre-evening meal time, and evening time.

As shown in FIG. 6, the CPU 181 starts up in response to the measurement subject inputting a power on instruction through the operating unit 14 (step S1), and, using the load detection unit 33, measures the body weight of the measurement subject who has stepped onto the upper surface cover unit 35 (see FIG. 1) (step S2). At this time, the CPU 181 calculates the body composition information based on the body impedance detected by the impedance detection unit 20 (see FIG. 2) using the electrode units 36 of the body weight measurement unit 30 and the electrode units 21 of the display/operating unit 10.

After this, the CPU 181 executes a storage/analysis process (step S3), turns the power off (step S4), and ends the processing.

FIG. 7 is a flowchart illustrating the storage/analysis process (see step S3 in FIG. 6). As shown in FIG. 7, the CPU 181 obtains data of the present day/time, which is the day/time of the body weight measurement in the aforementioned step S2, from the timer unit 13, and determines whether the present day/time corresponds to the morning time, the evening time, or the pre-evening meal time (step S21). It is assumed that data of the morning time and the evening time is held in advance in a memory within the control unit 18. The determination can be made by comparing the morning time and evening time data read out from the memory with the present day/time data.

If it is determined to be morning time ("morning" in step S21), the CPU 181 generates the record 40 using the body weight measured in step S23 as the morning body weight, and stores the generated record 40 in the storage unit 12. This record 40 includes the data 401 indicating the measured morning body weight, the data 403 indicating the present day/time, and the flag 404 indicating "morning".

When the record 40 is stored, the target obtainment unit 182 calculates the evening target body weight in accordance with the procedure illustrated in FIG. 5, and stores the evening target body weight in the storage unit 12 (step S24).

Figure 9A:
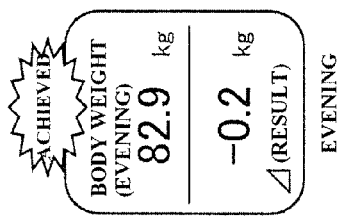
FIGS. 9A through 9F are diagrams illustrating display examples according to a preferred embodiment of the present invention.
Figure 9B:
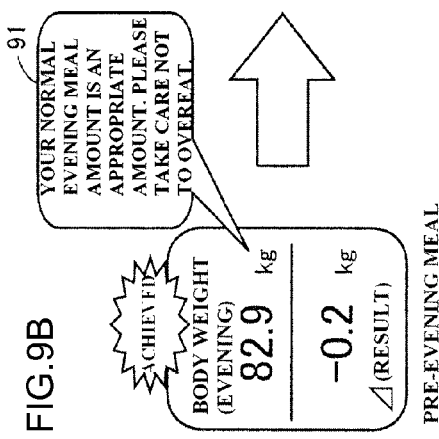
Figure 9C:
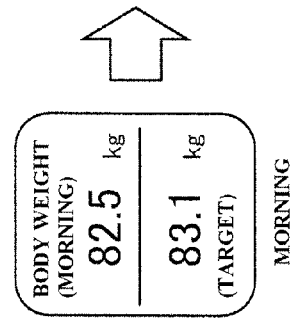
Figure 9D:
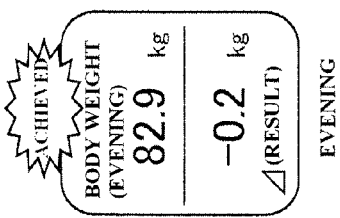

The output processing unit 186 displays a screen including display items of the calculated evening target body weight and the morning body weight measured in step S2 in the display unit 15 (step S25). FIGS. 9A and 9D illustrate examples of this display screen. The difference between the two body weights may further be calculated and displayed as display items in the screen at the same time, and in such a case, it is easier for the measurement subject to understand a guideline to achieve his/her target.

Next, the change amount calculation unit 190 calculates a nighttime change amount, and stores the data 405C indicating the calculated nighttime change amount in the record 40 in association with the morning body weight (step S26). The nighttime change amount 405C is calculated by subtracting yesterday's evening body weight from today's morning body weight. After this, the process returns to step S4 in FIG. 6.

In the case where the evening time has been determined in step S21 ("evening" in step S21), the CPU 181 stores the measured body weight obtained in step S2 in the record 40 as the evening body weight (step S27). Specifically, the data 401 indicating the measured evening body weight, the data 403 indicating the present day/time, and the flag 404 indicating "evening" are stored in the record 40.

When the evening body weight has been stored, the evaluation unit 184 evaluates the target achievement level based on the record 40 in the storage unit 12, and stores a result of the evaluation in the record 40 as the data 406 (step S28). Specifically, the evaluation unit 184 calculates a value by subtracting the evening target body weight calculated that day in step S24 from the measured evening body weight; if it is determined that the calculated value indicates 0 or a negative value, the target is evaluated as being achieved, whereas if it is determined that the value is greater than 0, the target is evaluated as not being achieved. When the target is evaluated as being achieved, "OK" is stored in the record 40 as the data 406, whereas when the target is evaluated as not being achieved, "NG" is stored in the record 40 as the data 406.

Figure 9E:
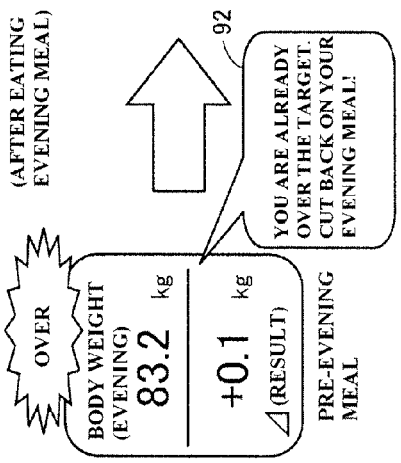
Figure 9F:
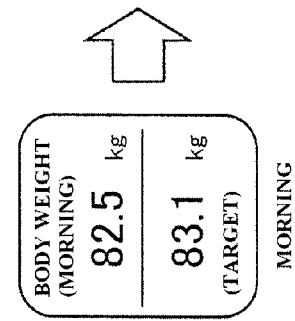

The output processing unit 186 displays a screen including the aforementioned evaluation result in the display unit 15 (step S29). FIGS. 9C and 9F illustrate examples of this display screen. These display screens include, as display items, the measured evening body weight, the aforementioned calculated value, and the evaluation result. In this example, the calculated value obtained by subtracting the evening target body weight from the evening body weight is less than 0 (−0.2 kg), and thus text reading "achieved" is displayed as the evaluation result. Note that the evening target body weight may be displayed at the same time, or may be displayed instead of the calculated value. Furthermore, the evaluation result maybe be outputted as audio. In the case where the calculated value is a positive value greater than 0 and the target has not been achieved, text reading "not achieved" is displayed instead of the text reading "achieved", or audio to that effect is outputted.

Although the evaluation is carried out by comparing the calculated value obtained by subtracting the evening target body weight from the evening body weight with a value of 0, the determination value used for the evaluation is not limited to 0.

Next, the change amount calculation unit 190 calculates an evening meal change amount 405B and an intra-day change amount 405A, and stores the calculated evening meal change amount 405B and intra-day change amount 405A in the record 40 (step S30). The evening meal change amount 405B is calculated by subtracting the pre-evening meal body weight from the evening body weight, and the intra-day change amount 405A is calculated by subtracting the morning body weight from the evening body weight. After this, the process returns to step S4 in FIG. 6.

Returning to step S21, when it is determined that the time corresponds to neither the morning time nor the evening time, or in other words, when it is determined to be "pre-evening meal" ("pre-evening meal" in step S21), the CPU 181 stores the measured body weight obtained in step S2 in the record 40 as the pre-evening meal body weight (step S31). Specifically, the data 401 indicating the measured body weight, the data 403 indicating the present day/time, and the flag 404 indicating "pre-evening meal" are stored in association with each other in the record 40.

The target achievement determination unit 189 then determines whether or not the target has been achieved (step S33). In other words, the evening target body weight is subtracted from the pre-evening meal body weight, and if that calculated value is less than or equal to 0, it is determined that the target has been "achieved" because the present body weight is not greater than the target evening body weight ("achieved" in step S34); the advice obtainment unit 185 then searches the data 46 and obtains "achieved" advice based on the result of the determination (step S35). On the other hand, if the calculated value is greater than 0, it is determined that the target is "not achieved" (over) because the evening target body weight has already been exceeded ("not achieved" in step S34); the advice obtainment unit 185 then searches the data 46 and obtains "not achieved" advice based on the result of the determination (step S36). The obtained advice is displayed by the output processing unit 186 in the display unit 15 (step S38, step S39). FIG. 9B illustrates an "achieved" screen as an example of the display screen, whereas FIG. 9E illustrates a "not achieved" screen. After the screen has been displayed, the processing returns to step S4 in FIG. 6.

In FIG. 9B, advice 91 saying "take care to eat a proper amount during evening meals and not to eat too much" is read out from the data 46 and outputted as audio, in addition to the "achieved" display. In FIG. 9E, advice 92 prompting the measurement subject to "eat less during the evening meal" is read out from the data 46 and outputted as audio, in addition to a display message indicating that the body weight is "over" the target. The advice 91 and 92 are not limited to audio, and may instead be displayed in the display unit 15.

Another method by which the target achievement determination unit 189 makes the determination (step S33) will now be described. Although the aforementioned process preferably uses the evening target body weight as a threshold value for the determination, the present invention is not limited thereto, and a threshold derived (calculated) from the target evening body weight may be used instead.

In the present preferred embodiment, a single record 40 is generated each day, and body weights measured in the morning, before the evening meal, and in the evening on that day are stored in that record 40. To facilitate the descriptions, FIG. 8A indicates changes in the measured body weight in time series based on the respective records 40 shown in FIG. 4A, FIG. 8B illustrates evening meal change amounts for each measurement day as a bar graph, and FIG. 8C illustrates the nighttime change amounts for each measurement day as a bar graph.

The target achievement determination unit 189 derives the threshold value to determine whether or not the target has been achieved using the evening meal change amount based on the evening meal change amount 405B in the records 40 stored in the storage unit 12 from a set period in the past. Specifically, a representative value is used for the evening meal change amount. Here, an average value is calibrated as the representative value, but the value is not limited to an average value, and may be a mode value, a median value, or the like. Note that when calculating the threshold value, the value of a typical evening meal change amount obtained in advance through experimentation may be used instead of the evening meal change amount unique to that measurement subject.

The target achievement determination unit 189 sets a reference for the determination based on the result of subtracting an average evening meal change amount from the evening target body weight. This setting procedure will be described with reference to FIG. 10.

As shown in FIG. 10, the target achievement determination unit 189 calculates a body weight value corresponding to 0% (here, this will be called a "0% body weight") in the case where the evening target body weight is associated with 100% (here, this will be called a "100% body weight") and the calculated value obtained by subtracting the average evening meal change amount from the target evening body weight is associated with 50%.

After calculating the 0% body weight, the target achievement determination unit 189 calculates body weights corresponding to 40% and 80% (here, these will be called a "40% body weight" and an "80% body weight") based on the 100% body weight and the 0% body weight. The body weights are then divided into multiple segments, with a rank P3 corresponding to greater than or equal to the 0% body weight and less than the 40% body weight, a rank P2 corresponding to greater than or equal to the 40% body weight and less than the 80% body weight, and a rank P1 corresponding to greater than or equal to the 80% body weight.

The target achievement determination unit 189 then determines whether the pre-evening meal body weight measured in step S31 corresponds to the rank P1, P2, or P3, and outputs the result of this determination to the advice obtainment unit 185.

The advice obtainment unit 185 then searches the data 46 based on the inputted determination result, and reads out, from the data 46, advice associated in advance with the corresponding rank segment. Here, advice M1 through M3 illustrated in FIGS. 11A through 11C, corresponding to the respective ranks P1, P2, and P3, are obtained.

Because the pre-evening meal body weight is greater than or equal to the 80% body weight and, depending on the evening meal amount, there is a high likelihood that the evening target body weight will be exceeded, the advice M1 includes advice related thereto (that is, that there is a chance the target evening body weight will be exceeded, to reduce the evening meal amount, to exercise after the meal, and so on). Meanwhile, because the pre-evening meal body weight is greater than or equal to the 40% body weight and less than the 80% body weight and there is thus no chance that the evening target body weight will be exceeded of the measurement subject does not overeat (that is, that it is possible to achieve the target), the advice M2 includes advice related thereto (that is, that the measurement subject may achieve the target, to avoid overeating and take care to eat a proper amount, and so on). Furthermore, because the pre-evening meal body weight is greater than or equal to the 0% body weight and less than the 40% body weight and thus the body weight is being managed successfully (that is, that it is highly likely that the target will be achieved), the advice M3 includes advice related thereto (that the body weight is being managed successfully, that the measurement subject should take care not to lose too much weight, and so on). These pieces of advice may be outputted as audio.

FIGS. 12A and 12B illustrate a display example of the advice M1 shown in FIG. 11A. In FIG. 12A, the morning body weight measured in the morning (50.7 kg) is displayed along with the evening target body weight (51.3 kg). A display example of the pre-evening meal measurement for this case is illustrated in FIG. 12B. In FIG. 12B, the measured pre-evening meal body weight (51.2 kg) is displayed along with the advice M1.

By confirming the advice M1 to M3 at the pre-evening meal measurement, the measurement subject can understand an evening meal amount (that is, an appropriate amount) to achieve the target.

Although the three ranks illustrated in FIG. 10 are described as being allocated when obtaining the advice outputted at the pre-evening meal measurement, the allocation of ranks is not limited thereto. For example, it may be determined whether or not a condition ((pre-evening meal body weight+average evening meal change amount)>evening target body weight) holds true, and in the case where the result of the determination indicates that the condition holds true, advice notifying the measurement subject that the target may not be achieved may be outputted, whereas in the case where the condition does not hold true, advice notifying the measurement subject that the target may be achieved and that the body weight management is successful may be outputted.

In this manner, various types of methods can be applied in the determination method of step S33, and the method used in the determination can be changed.

Figure 13A:
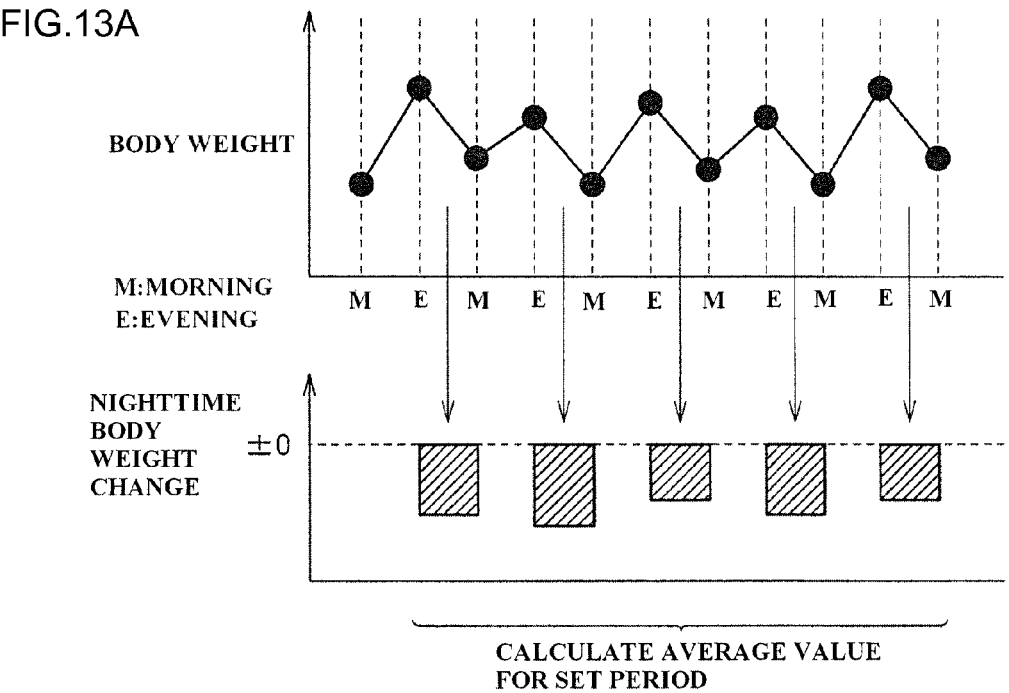
FIGS. 13A and 13B are diagrams illustrating an intra-day variation in a body weight.

In the present preferred embodiment, the standard intra-day variation amount data 41 can be accurately set on a measurement subject-by-measurement subject basis. In other words, as shown in FIG. 13A, a body weight change amount during sleep is calculated by subtracting the measurement subject's morning body weight from the evening body weight, and by calculating an average value for multiple days' worth of the body weight change amount during sleep, the standard intra-day variation amount data 41 can be determined based on the measurement subject's actual body weight increase/decrease amount.

Furthermore, by using this calculation method, the correct standard intra-day variation amount can be determined regardless of whether the body weight is in an increasing trend or a decreasing trend.

Figure 13B:
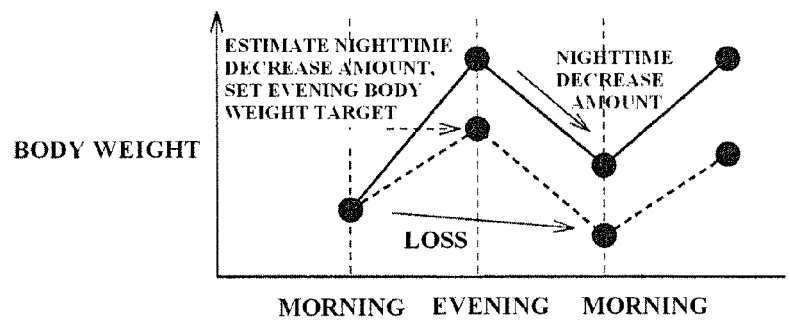

Furthermore, in the present preferred embodiment, the tendency for a person's body weight to increase from morning to evening and decrease from evening to morning (see FIG. 5A and FIG. 13B) is taken into consideration, and by calculating and outputting the evening target body weight, which is a guideline for the degree to which the increase from the morning time to the evening time should be suppressed, the measurement subject can obtain information regarding an appropriate evening meal amount, as well as support information for managing increases/decreases in his/her body weight on a daily basis.

Through the aforementioned configurations and operations, the measurement subject can confirm the evening target body weight and an appropriate evening meal amount, which indicate the degree to which the intra-day body weight variation should be controlled, and can manage his/her intra-day body weight variations in a deliberate manner so as to achieve the target. Accordingly, in the case where, for example, the measurement subject wishes to lose weight, the measurement subject can obtain information to determine whether or not the weight loss is proceeding successfully on a day-by-day basis, which is a short amount of time, as well as information regarding eating habits for supporting the weight loss.

In the aforementioned presentation of advice (step S38, step S39), advice may be given regarding the food content of the evening meal as described hereinafter, in addition to the amount of the evening meal.

At each evening meal, the measurement subject captures an image of the food content (a menu or the like) that he/she will eat at the evening meal using the camera unit 6, and sends that image data to the server 5. Meanwhile, the CPU 181 sends data indicating the result of the evaluation ("OK" or "NG") performed by the evaluation unit 184 in the aforementioned step S28 based on each day's evening body weight to the server 5, and also sends data of the result of the determination performance step S34 to the server 5. This determination result is indicated by a flag F, and the value of the flag F indicates "achieved" or "not achieved".

Each day, the CPU 521 of the server 5 associates the image data of the evening meal received from the camera unit 6 and the evaluation result and determination result received from the body weight/body composition meter 3 with a reception date/time for these pieces of information as measured by the timer 50, and stores the information in the storage unit 55 as the record 551. As a result, the food content of each evening meal is stored in the storage unit 55 in association with information as to whether or not the evening body weight target has been achieved and information as to whether or not the pre-evening meal body weight target has been achieved. Accordingly, image data in a record 551 in which an evaluation result of "OK" is stored corresponds to food content indicating a pattern of success in which the evening body weight target is achieved. Here, it is assumed that a sufficient number of records 551 are already stored in the storage unit 55.

In step S36 of the operations, the advice obtainment unit 185 sends, to the server 5, a request signal requesting "information on excessive pre-evening meal weights". Upon receiving the request, the server 5 searches the storage unit 55 based on the received request, reads out the image data from the records 551 in which the evaluation result indicates "OK" and the flag F indicates "not achieved" based on the result of the search, and returns the read-out image data to the body weight/body composition meter 3. In the body weight/body composition meter 3, the advice obtainment unit 185 displays the image data received from the server 5 in the display unit 15 in step S39. Through this, the measurement subject can obtain advice on food content for a pattern of success through which he/she can achieve the target evening body weight.

Meanwhile, the server 5 may read out the image data from the records 551 in which the evaluation result indicates "NG" and the flag F indicates "not achieved" based on the result of the search, and the read-out image data may be displayed. In this case, the measurement subject can be provided with food content that he/she should avoid in order to achieve the target evening body weight.

In step S35, the advice obtainment unit 185 sends, to the server 5, a request signal requesting "information on achieving pre-evening meal weights". Upon receiving the request, the server 5 searches the storage unit 55 based on the received request, reads out the image data from the records 551 in which the evaluation result indicates "OK" and the flag F indicates "achieved" based on the result of the search, and returns the read-out image data to the body weight/body composition meter 3. In the body weight/body composition meter 3, the advice obtainment unit 185 displays the image data received from the server 5 in the display unit 15 in step S38. Through this, the measurement subject can obtain advice on food content for a pattern of success through which he/she can achieve the target evening body weight.

Meanwhile, the server 5 may read out the image data from the records 551 in which the evaluation result indicates "NG" and the flag F indicates "achieved" based on the result of the search, and the read-out image data may be displayed. In this case, the measurement subject can be provided with food content that he/she should avoid in order to achieve the target evening body weight.

In this manner, food content for a pattern of success in which the target evening body weight can be achieved is displayed prior to the evening meal, and it is thus possible to provide the measurement subject with accurate advice to support his/her body weight management from the standpoint of meals. Furthermore, because the images that are provided are captured images of food content, the measurement subject can also confirm a menu, ingredients used in the preparation, and the amount based on the images.

Furthermore, if a comment (regarding an amount of flavoring, seasonings used, ingredients, amounts, and so on) is made when the image of the food content is captured, inputting the comment using the operating unit 53 and storing the details thereof in the record 551 makes it possible to display the comment to the measurement subject along with the captured image.

Note that the image of and comment regarding the food content may be displayed by the display unit 54 of the server 5.

The method for calculating the evening target body weight is not limited to the calculation method indicated in step S24. For example, an average of the nighttime change amounts (called an "average nighttime change amount") may be calculated based on the nighttime change amount 405C in the records 40 from a set period in the past indicated in FIG. 4D, and the evening target body weight may then be calculated by adding the morning body weight and the average nighttime change amount. Note that when performing this calculation, a median value or a mode value may be used instead of an average value of the nighttime change amount 405C.

Although the body weight/body composition meter 3 preferably performs all the computations in the aforementioned preferred embodiment, the configuration may be such that the server 5 carries out various types of computations, outputs, and so on.

In this case, the configuration may be such that the body weight/body composition meter 3 sends the body weight measurement values along with the measurement day/time to the server 5 in step S3. The configuration may be such that upon receiving the body weight measurement values and the measurement day/time from the body weight/body composition meter 3, the CPU 521 in the control unit 52 of the server 5 obtains the records 40 including the morning body weight and the evening body weight, and executes the processes according to the flowcharts in FIGS. 6 and 7, after which the data is stored in the storage unit 55, and the display is carried out in the display unit 54. In this case, the server 5 may send the information displayed in the screen of the display unit 54 to the body weight/body composition meter 3, and the body weight/body composition meter 3 may receive this information and display the received information in the display unit 15.

In this manner, even in the case where processing is carried out by the server 5, the measurement subject can be notified of the evening target body weight and the results of determining the degree of achievement. In addition, in the case where the server 5 is used in this manner, it is also possible for a body weight management counselor or the like to confirm the information and offer advice to a user.

The configuration may be such that the measurement subject makes an input by selecting a morning/evening button (not shown) in the operating unit 14 between step S1 and step S2. In this case, the morning body weight measurement and the evening body weight measurement can be distinguished based on the input. Accordingly, the body weight management device according to the present preferred embodiment can also be used by a measurement subject whose sleeping and waking times are inverted, such as a shift worker.

In the case where this configuration is used, the display content may be varied depending on whether or not the morning/evening button has been depressed, such as displaying only the body weight and not displaying targets or the like if the morning/evening button has not been depressed. Accordingly, the measurement subject can be prevented from forgetting to press the morning/evening button.

In addition, although the aforementioned preferred embodiment describes the basal metabolism amount being calculated based on the measurement subject's body impedance as detected by the impedance detection unit 20, the calculated body composition information is not limited to the basal metabolism amount. For example, a body fat percentage, BMI, visceral fat level, skeletal muscle percentage, body age, and so on may be calculated based on the body impedance, the height, age, and sex of the measurement subject stored in the storage unit 12, and the body weight detected by the load detection unit 33, and that calculated information may be outputted along with the body weight.

Although the aforementioned preferred embodiment describes an image being captured of only the food content of the evening meal, images may be captured of the food content for a morning meal, a midday meal, and an evening meal, and images of the morning, midday, and evening food content on days for which the evening body weight target is determined to be achieved ("OK") may then be displayed. Alternatively, images of the morning, midday, and evening food content on days for which the evening body weight target is determined to not have been achieved ("NG") may be displayed. Through this, it is possible to provide information leading to successful body weight management, based on trends in the food content of the measurement subject.

In addition, the server 5 may store information (a menu or the like) of food content likely to lead to an increase in body weight and information of food content unlikely to lead to an increase in body weight in the storage unit 55, and may send this information to the body weight/body composition meter 3 during the processes in step S35 and step S36.

The stated body weight management method carried out by the body weight/body composition meter 3 according to the present preferred embodiment can also be provided as a program. This program can also be recorded on a computer-readable recording medium, such as a flexible disk provided to the computer of the control unit 18 or the control unit 52, a CD-ROM (compact disk read-only memory), a ROM, a RAM, a memory card, and so on, and can then be provided as a program product. Alternatively, the program can be recorded on a recording medium such as a hard disk mounted within a computer, and can be provided in such form as a program. Further still, the program can also be downloaded via a network, and can be provided in such form as a program.

The provided program product is installed in a program storage unit such as a hard disk or the like and is then read out and executed by the CPU 181 (or 521). Note that the program product includes the program itself and the recording medium on which the program is recorded.

Note that the preferred embodiments disclosed above are to be understood as being in all ways exemplary and in no way limiting. The scope of the present invention is defined not by the aforementioned descriptions of various preferred embodiments but by the scope of the appended claims, and all changes that fall within the same essential spirit as the scope of the claims are intended to be included therein as well.

The invention claimed is:
1. A body weight management device comprising:
a body weight obtainment unit that obtains measurement data in which a body weight measurement for a measurement subject and a measurement day/time are associated with each measurement, the measurement data including a post-waking body weight at a first timing after the measurement subject wakes, a pre-sleep body weight at a second timing before the measurement subject sleeps, and a pre-meal body weight at a third timing prior to a meal eaten by the measurement subject;
an increase/decrease amount calculation unit that calculates a target intra-day change amount based on a nighttime body weight decrease obtained from the measurement data which is an amount by which the body weight decreases during sleep;
a target obtainment unit that, based on the target intra-day change amount and the post-waking body weight, calculates an evening target body weight which is a targeted pre-sleep body weight to be obtained at the second timing;
an advice obtainment unit that obtains advice information regarding meals to achieve the evening target body weight, based on a result of comparing the pre-meal body weight measured at the third timing with a threshold value; and
an output unit that outputs the obtained advice information.

2. The body weight management device according to claim 1, wherein the advice obtainment unit derives the threshold value using the evening target body weight.

3. The body weight management device according to claim 2, wherein the advice obtainment unit calculates differences between the pre-meal body weight and the pre-sleep body weight for each day from multiple pieces of obtained measurement data, and calculates the threshold value based on the calculated differences and the evening target body weight.

4. The body weight management device according to claim 3, wherein
the advice obtainment unit includes a segmentation unit that segments body weights in predetermined ranges including the evening target body weight and the threshold value into multiple ranges;
different pieces of the advice information are associated with each of the ranges into which the body weights are segmented; and
the advice obtainment unit obtains the advice information associated with a range, of the multiple ranges, to which the pre-meal body weight belongs.

5. The body weight management device according to claim 3, wherein
a representative value is calculated for the calculated differences; and
the threshold value is calculated by subtracting the representative value from the evening target body weight.

6. The body weight management device according to claim 1, wherein the increase/decrease amount calculation unit calculates the target intra-day change amount based on an intra-day target increase/decrease amount of the body weight and the nighttime body weight decrease.

7. The body weight management device according to claim 1, wherein the advice information includes information regarding a meal amount.

8. The body weight management device according to claim 1, wherein the advice information includes information regarding meal content.

9. The body weight management device according to claim 8, further comprising:
an image obtaining unit that obtains an image obtained by capturing an image of each meal after the third timing; and
a determination unit that determines whether or not an intra-day target has been achieved based on the pre-sleep body weight and the evening target body weight; wherein
the information regarding the meal content includes the image obtained by capturing an image of the meal.

10. The body weight management device according to claim 9, wherein the information regarding the meal content includes, of the images obtained by capturing images of the meals, images obtained by capturing images of the meals on days when it has been determined that the intra-day target has been achieved.

11. A body weight management method that manages a measurement subject's body weight using a computer, the method comprising:
obtaining measurement data in which a body weight measurement of the measurement subject and a measurement day/time are associated with each measurement, the measurement data including a post-waking body weight at a first timing after the measurement subject wakes, a pre-sleep body weight at a second timing before the measurement subject sleeps, and a pre-meal body weight at a third timing prior to a meal eaten by the measurement subject;
storing the measurement data in a memory;
reading out the measurement data from the memory and calculating a target intra-day change amount based on a nighttime body weight decrease obtained from the read-out measurement data which is an amount by which the body weight decreases during sleep;
calculating, based on the target intra-day change amount and the post-waking body weight, an evening target body weight which is a targeted pre-sleep body weight to be obtained at the second timing;
obtaining advice information regarding meals to achieve the evening target body weight, based on a result of comparing the pre-meal body weight measured at the third timing with a threshold value; and
outputting the obtained advice information.

12. A non-transitory computer-readable medium including a computer program for causing a computer to execute a body weight management method, the method comprising:
obtaining measurement data in which a body weight measurement of the measurement subject and a measurement day/time are associated with each measurement, the measurement data including a post-waking body weight at a first timing after the measurement subject wakes, a pre-sleep body weight at a second timing before the measurement subject sleeps, and a pre-meal body weight at a third timing prior to a meal eaten by the measurement subject;
storing the measurement data in a memory;
reading out the measurement data from the memory and calculating a target intra-day change amount based on a nighttime body weight decrease obtained from the read-out measurement data which is an amount by which the body weight decreases during sleep;
calculating, based on the target intra-day change amount and the post-waking body weight, an evening target body weight which is a targeted pre-sleep body weight to be obtained at the second timing;
obtaining advice information regarding meals to achieve the evening target body weight, based on a result of comparing the pre-meal body weight measured at the third timing with a threshold value; and
outputting the obtained advice information.

13. A body weight management system comprising:
a measurement device that measures body information of a measurement subject; and
an information processing device; wherein
the measurement device includes:
a body weight obtainment unit that measures a body weight of the measurement subject; and
an output unit that outputs measurement data in which a body weight measurement and a measurement day/time are associated with each measurement, the measurement data including a post-waking body weight at a first timing after the measurement subject wakes, a pre-sleep body weight at a second timing before the measurement subject sleeps, and a pre-meal body weight at a third timing prior to a meal eaten by the measurement subject; and
the information processing device includes:
a receiving unit that receives the measurement data outputted from the measurement device;
an increase/decrease amount calculation unit that calculates a target intra-day change amount f based on a nighttime body weight decrease obtained from the measurement data which is an amount by which the body weight decreases during sleep;

a target obtainment unit that, based on the target intraday change amount and the post-waking body weight, calculates an evening target body weight which is a targeted pre-sleep body weight to be obtained at the second timing;

an advice obtainment unit that obtains advice information regarding meals to achieve the evening target body weight, based on a result of comparing the pre-meal body weight measured at the third timing with a threshold value; and an output unit that outputs the obtained advice information.

* * * * *